United States Patent
Santa et al.

(10) Patent No.: US 6,448,413 B1
(45) Date of Patent: Sep. 10, 2002

(54) PROCESS FOR THE SYNTHESIS OF A-NOR-SECO COMPOUNDS WITH STERANE SKELETON

(75) Inventors: Csaba Santa; Zoltan Tuba; Sandor Maho; Janos Szeles; Gabor Balogh; Janos Brlik; Ferenc Trischler; Gabriella Szilagyi; Erika Bakcsi, all of Budapest (HU)

(73) Assignee: Richter Gedeon Vegyeszeti Gyar Rt., Budapest (HU)

( * ) Notice: Subject to any disclaimer, the term of this patent is extended or adjusted under 35 U.S.C. 154(b) by 0 days.

(21) Appl. No.: 10/030,743

(22) PCT Filed: May 26, 2000

(86) PCT No.: PCT/HU00/00047

§ 371 (c)(1),
(2), (4) Date: Nov. 30, 2001

(87) PCT Pub. No.: WO00/76968

PCT Pub. Date: Dec. 21, 2000

(30) Foreign Application Priority Data

Jun. 10, 1999 (HU) .............................. 9901939

(51) Int. Cl.⁷ ................. C07D 209/36; C07C 59/147; C07C 62/14
(52) U.S. Cl. ..................... 548/484; 562/499
(58) Field of Search ................ 548/484; 562/499

(56) References Cited

U.S. PATENT DOCUMENTS 3,128,283 A    4/1964   Pappo et al. ............ 549/268
3,280,133 A  * 10/1966  Pappo et al. ............ 546/77

OTHER PUBLICATIONS

Bi et al., Chemical Abstracts, Columbus Ohio, vol. 117, No. 20715, XP–002149884 Studies on Anabolic Steriods.

\* cited by examiner

*Primary Examiner*—Fiona T. Powers

(74) *Attorney, Agent, or Firm*—Herbert Dubno; Jonathan Myers

(57) ABSTRACT

The invention relates to a new process for the synthesis of 17β-hydroxy-17α-methyl-1,3-seco-2-nor-5α-androstane-3-acid derivatives of formula (I)

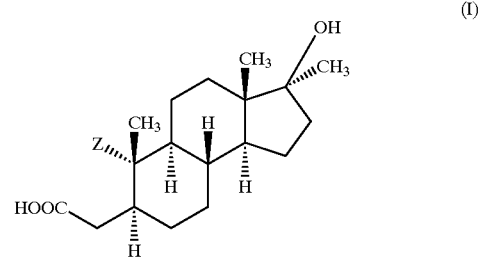

(I)

wherein the meaning of Z is carboxyl or formyl group and to the new secoindoxylidene carboxylic acid derivatives of formula (II)

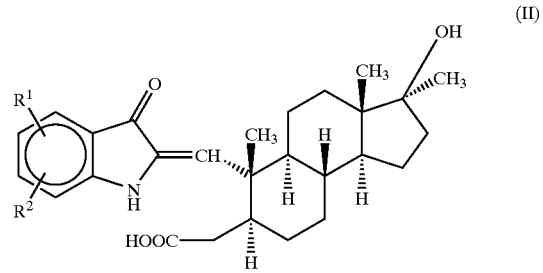

(II)

wherein $R^1$ and $R^2$ independently are $C_1$–$C_4$ alkyl or alkoxy group, hydrogen or halogen atom—which are intermediates for preparing the compounds of formula (I).

The 17β-hydroxy-17α-methyl-1,3-seco-2-nor-5α-androstane-3-acid derivatives of formula (I) are intermediates in the synthesis of oxandrolon (17β-hydroxy-17α-methyl-2-oxa-5α-androstane-3-one), which is used as anabolic in therapy.

11 Claims, No Drawings

PROCESS FOR THE SYNTHESIS OF A-NOR-SECO COMPOUNDS WITH STERANE SKELETON

The invention relates to a new process for the synthesis of 17β-hydroxy-17α-methyl-1,3-seco-2-nor-5α-androstane-3-acid derivatives of formula (I)

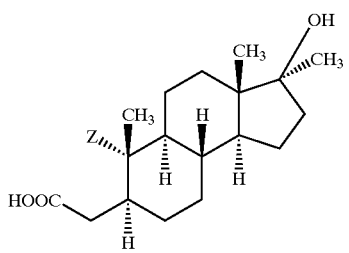

(I)

wherein the meaning of Z is carboxyl or formyl group and to the new secoindoxylidene carboxylic acid derivatives of formula (II)

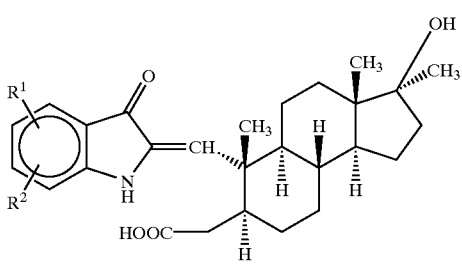

(II)

wherein $R^1$ and $R^2$ independently are $C_1$–$C_4$ alkyl or alkoxy group, hydrogen or halogen atom—which are intermediates for preparing the compounds of formula (I).

The 17β-hydroxy-17α-methyl-1,3-seco-2-nor-5α-androstane-3-acid derivatives of formula (I) are intermediates in the synthesis of oxandrolon (17β-hydroxy-17α-methyl-2-oxa-5α-androstane-3-one), which is used as anabolic in therapy. The oxandrolone is used in pediatrics and for mitigation of loss of weight developing as a consequence of infections. traumas and surgical intervention. Recently the therapeutic use was extended to the improvement of the condition of AIDS patients.

Although the 17β-hydroxy-17α-methyl-1,3-seco-2-nor-5α-androstane-3-acid derivative of formula (I). wherein the meaning of Z is carboxyl group. is described in the literature [J. Steroid Biochem. Molec. Biol. 42(2). 229–242 (1992)] as the metabolite of oxymethalone (17β-hydroxy-2-hydroxymethylene-17α-methyl-5α-androstane-3-one) and its structure was proved by GC-MS method via a derivative of it. its synthesis and physical properties are not known.

The secoindoxylidene carboxylic acid type compounds of formula (II) are new.

The 17β-hydroxy-17α-methyl-1,3-seco-2-nor-5α-androstane-3-acid derivative of formula (I), wherein meaning of Z is formyl group. is known, its synthesis is described in several patents, i.e. the U.S. Pat. Nos. 3.101, 349, 3,128,283 and 3,155,684, the German patent No. 1.171.425 and the French patent No. M1697. These patents describe the oxidation of 17β-hydroxy-17α-methyl-5α-androst-1-ene-3-one with lead tetraacetate in the presence of osmium tetroxide, when 17β-hydroxy-17α-methyl-1-oxo-1, 3-seco-2-nor-5α-androstane-3-acid is obtained. The descriptions do not give yields. The use of lead tetraacetate and especially the osmium tetroxide is extremely dangerous for health and not environmental friendly. An other difficulty is that the synthesis of the starting material, the 17β-hydroxy-17α-methyl-5α-androst-1-ene-3-one, can be carried out only in low yield by bromination of 17β-hydroxy-17α-methyl-5α-androstane-3-one and subsequent hydrogen bromide elimination. This procedure is described i.e. in the U.S. Pat. No. 3128,283. According to the U.S. Pat. No. 3.109,016 the oxidation of the above mentioned starting material is carried out by ozone in carbon tetrachloride at −20° C. to yield the mixed anhydride of 17β-hydroxy-17α-methyl-1-oxo-1,3-seco-2-nor-5α-androstane-3-acid formed with formic acid. The oxidation was also carried out in dichloromethane in the presence of methanol to yield the methyl ester of the seco compound. The procedure does not give yields. As the use of carbon tetrachloride is restricted because of its harmful effect to health, the synthesis can not be used on industrial scale.

As can be seen from the state of arts despite the fact that there is a need for the compounds of formula (I), there is no such procedure for the synthesis of them. which can be carried out on industrial scale in good yield and without using dangerous reagents.

Surprisingly it was found, that the 17β-hydroxy-17α-methyl-1,3-seco-2-nor-5α-androstane-3-acid derivatives of formula (I), known only as metabolites or intermediates, can be synthesized from 17β-hydroxy-17α-methyl-5α-androstane-3-one of formula (III)

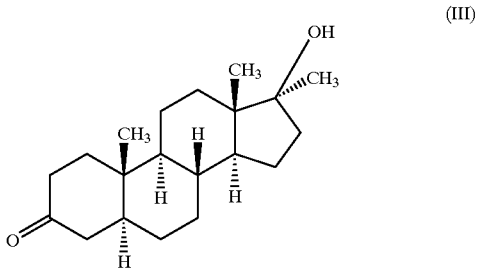

(III)

known as mestanolone [Helv. Chim: Acta, 30(3), 867–878, (1947)]—by an industrially applicable method according to our invention as follows:

The 17β-hydroxy-17α-methyl-5α-androstane-3-one of formula (III) is reacted with an aromatic nitro-aldehyde of formula (IV)

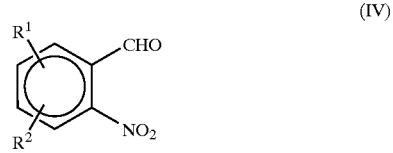

(IV)

wherein $R^1$ and $R^2$ independently are $C_1$–$C_4$ alkyl or alkoxy group, hydrogen or halogen atom—in a $C_1$–$C_4$ alcohol in the presence of aqueous alkali metal hydroxide solution, the obtained secoindoxylidene carboxylic acid derivative of formula (II)

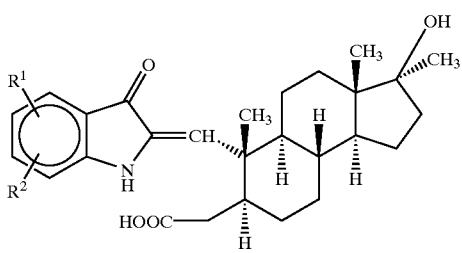

(II)

wherein the meaning of $R^1$ and $R^2$ as defined above—is separated from the reaction mixture after acidifying in given case is recrystallized from a $C_1$–$C_4$ alcohol or $C_3$–$C_5$ ketone. and oxidized using
i) for the synthesis of 17β-hydroxy-17α-methyl-1,3-seco-2-nor-5α-androstane-3-acid derivative of formula (I), wherein Z is carboxyl group, at 15–40° C. 2.5–5 mol equivalent, or
ii) for the synthesis of 17β-hydroxy-17α-methyl-1,3-seco-2-nor-5α-androstane-3-acid derivative of formula (I), wherein Z is formyl group, at 15–30° C. 1–1.5 mol equivalent alkali metal permanganate in a mixture of $C_1$–$C_5$ alcohol or $C_3$–$C_6$ ketone and aqueous alkali metal hydroxide.

The reaction of mestanolone of formula (III) and aromatic nitro-aldehyde of formula (IV) is preferably carried out in methanol as $C_1$–$C_4$ alcohol in the presence of potassium hydroxide. The mestanolone is preferably suspended in the mixture of the alcohol type solvent and the aqueous alkali metal hydroxide and the aromatic nitro-aldehyde of formula (IV) in alcoholic solution is added to the reaction. The addition can be carried out between 0° C. and the reflux temperature of the reaction mixture. The completion time of the reaction depends on the temperature.

After completion of the reaction the mixture was acidified with a diluted inorganic acid till pH=0–2.5. diluted with water, the precipitated yellow crystals were filtered off, washed with aqueous alcohol and dried. The obtained secoindoxylidene carboxylic acid of formula (II), the substance content of which is 80–95%, is recrystallized in given case from a $C_1$–$C_4$ alcohol or $C_3$–$C_5$ ketone.

The recrystallized or the crude secoindoxylidene carboxylic acid of formula (II) is dissolved in a mixture of $C_1$–$C_5$ alcohol or $C_3$–$C_6$ ketone, water and aqueous alkali metal hydroxide solution (pH=10–14) and for the synthesis of 17β-hydroxy-17α-methyl-1,3-seco-2-nor-5α-androstane-3-acid derivative of formula (I), wherein Z is carboxyl group, 2.5–5 mol equivalent of alkali metal permanganate in aqueous solution is added to the reaction at 15–40° C. The required temperature of 15–40° C. is kept with cooling. As the reaction proceeds the mixture turns brown. due to the precipitation of the manganese dioxide. After addition of the reagent the pH is checked and in case of deviation it is adjusted to the required value by addition of further alkali metal hydroxide solution. After completion of the reaction the precipitated manganese dioxide is filtered off or is dissolved with the addition of a reductive agent. i.e. sodium sulfite. the pH of the solution is adjusted to 5.5–6.5 and concentrated. The possible impurities precipitated from the concentrated solution are filtered off, the pH of the filtrate (which contains the desired product) is adjusted to 0–2.5 with addition of acid. The precipitated product is filtered off, washed with water and dried. The crude product is purified be suspending and stirring it in a halogenated alkan or in a mixture of a halogenated alkan and a ketone or in a ketone type solvent and subsequent filtration or recrystallization from a ketone type solvent.

If the above mentioned oxidation step is carried out the following way, instead of 17β-hydroxy- 17α-methyl-1,3-seco-2-nor-5α-androstane-3-acid derivative of formula (1), wherein Z is carboxyl group, the 17β-hydroxy- 17α-methyl-1,3-seco-2-nor-5α-androstane-3-acid derivative of formula (I), wherein Z is formyl group, is obtained. The reaction is carried out the same way as in the synthesis of 17β-hydroxy-17α-methyl-1,3-seco-2-nor-5α-androstane-3-acid derivative of formula (I), wherein Z is carboxyl group, with the difference that the temperature of the oxidation is 15–30° C. instead of 15–40° C. and 1-1.5 mol equivalent of alkali metal permanganate is used instead of 2.5–5 mol equivalent. The crude product is purified by recrystallization from acetonitrile or from a ketone type solvent.

The oxidative cleavage of the $C_1$–$C_2$ double bond of secoindoxylidene carboxylic acid derivatives of formula (II) is preferably carried out in acetone, ethanol or tertiary-butanol using sodium hydroxide as base. Both oxidation reactions are preferably carried out at 20–30° C.

The procedure according to the invention is illustrated in detail by the following not limiting examples.

EXAMPLE 1

17β-Hydroxy-17α-methyl-1-(1,3-dihydro-3-oxo-2H-indol-2-ylidene)-1,3-seco-2-nor-5α-androstane-3-acid 27.6 g (490 mmol) of potassium hydroxide in 60 cm³ of water is added to 1040 cm³ of methanol, then 50 g (164.2 mmol) of mestanolone is suspended in the so obtained solution. 25 g (165.4 mmol) of 2-nitro-benzaldehyde in 210 cm³ of methanol is added to the reaction mixture over a period of 15 min. keeping the temperature at 25–30° C. with cooling. After the addition of the reagent the starting material slowly dissolves and the colour of the reaction mixture turns yellow. The mixture is stirred at 20–30° C. for 3 h. then checked by thin layer chromatography. After completion of the reaction it is cooled to 10–15° C. and 200 cm³ (548.5 mmol) of 10% hydrochloric acid was added over a period of 15 min keeping the temperature below 20° C. During the addition of the hydrochloric acid the product starts to precipitate. Then 2500 cm³ of water is added to the reaction mixture and it is stirred for 3.0 min. The precipitated yellow crystals are filtered off. washed with water and dried at 50° C. till the weight was constant to yield 72.6 g, (96%. calculated for water free compound) of crude title compound. Alp: 170–190° C. Water content: 5%.

70 g (66.5 g of water free compound) of the above crude product is recrystallized from 4760 cm³ of methanol to yield 59.36 g (89.3%, calculated for water free starting material) of crystalline product. Mp: 184–190° C. $[\alpha]_D^{25}$: +105.4° (c=1, acetone).

EXAMPLE 2

17β-Hydroxy-17α-methyl-1-(1,3-dihydro-3-oxo-2H-indol-2-ylidene)-1,3-seco-2-nor-5α-androstane-3-acid 332 g (5.92 mol) of potassium hydroxide in 730 cm³ of water is added to 9.4 dm³ of methanol, then 600 g (1.97 mol) of mestanolone is suspended in the so obtained solution. 300 g (1.98 mol) of 2-nitro-benzaldehyde in 2.4 dm³ of methanol is added to the reaction mixture over a period of 10 min. After the addition of the reagent the starting material slowly dissolves and the colour of the reaction mixture turns yellow. The mixture is refluxed for 1 h, then checked by thin layer chromatography. After completion of the reaction it is cooled to 15° C. and 2.6 dm$^3$ of 10% sulfuric acid is added over a period of 15–20min keeping the temperature below 20° C. Then 24 dm$^3$ of water is added to the reaction mixture and it is stirred for 30 min (pH=2). The precipitated yellow crystals are filtered off, washed with a 3:1 mixture of water and methanol and dried at 50° C. till the weight was constant to yield 902.5 g (95.2%. calculated for water free compound) of crude title compound. Mp: 178–190° C. Water content: 5.3%.

EXAMPLE 3

17β-Hydroxy-17α-methyl-1-(5-chloro-1,3-dihydro-3-oxo-2H-indol-2-ylidene)-1,3-seco-2-nor-5α-androstane-3-acid 1.6 g (28.5 mmol) of potassium hydroxide is dissolved in a mixture of 4 cm$^3$ of water and 45 cm$^3$ of methanol, then 3 g (9.85 mmol) of mestanolone is added. 2.3 g (10.5 mmol) of 5-chloro-2-nitro-benzaldehyde (technical quality, about 85%) in 25 cm$^3$ of methanol is added to the basic reaction mixture. The mixture is stirred for 3 h. then checked by thin layer chromatography. After completion of the reaction it is cooled to 10–15° C. and 12 cm$^3$ of 10% hydrochloric acid is added, then it is diluted with 100 cm$^3$ of water. After stirring for 20 min, the precipitated crystals are filtered off, washed with 10 cm$^3$ of water and dried at 50° C. The obtained 4.8 g of crude product is crystallized from a mixture of dichloromethane/acetonitril to yield 3.1 g (66.7%) of the title compound. Mp: 215–217° C. (decomposes).

EXAMPLE 4

17β-Hydroxy-17α-methyl-1,3-seco-2-nor-5α-androstane-1,3-diacid 5 g (11.4 mmol) of crude 17β-hydroxy-17α-methyl-1-(1,3-dihydro-3-oxo-2H-indol-2-ylidene)-1,3-seco-2-nor-5α-androstane-3-acid, obtained in Example 2 is dissolved in 40 cm$^3$ of aceton and 0.8 g (20 mmol) of sodium hydroxide in 40 cm$^3$ of water is added. 2.7 g (17.1 mmol. 1.5 equivalent) of potassium permanganate in 45 cm$^3$ of water is added to the reaction mixture over a period of 30 min. keeping the temperature at 20–30° C. After stirring for 15 min, the precipitated manganese dioxide is filtered off and washed with 40 cm$^3$ of a 1:3 mixture of acetone-water. The filtrate is neutralized with 5 cm$^3$ of 10% sulfuric acid is (pH~6–7), then the acetone is evaporated at diminished pressure. The residue is cooled to 15–20° C. and acidified with 12 cm$^3$ of 10% sulfuric acid (pH~2). The crystalline solution is stirred for 20 min. then filtered, washed with water and dried at 50° C. till the weight is constant to yield 1.9 g (51.6%) of the title compound. Mp: 166–173° C.

EXAMPLE 5

17β-Hydroxy-17α-methyl-1,3-seco-2-nor-5α-androstane-1,3-diacid 5 g (11.4 mmol) of crude 17β-hydroxy-17α-methyl-1-(1, 3-dihydro-3-oxo-2H-indol-2-ylidene)-1,3-seco-2-nor-5α-androstane-3-acid, obtained in Example 2, is added to a mixture of 0.8 g (20 mmol) of sodium hydroxide in 40 cm$^3$ of water and 50 cm$^3$ of ethanol. 5.4 g (34.2 mmol, 3.0 equivalent) of potassium permanganate in 90 cm$^3$ of water is added to the reaction mixture over a period of 30 min, keeping the temperature at 20–30° C. After stirring for 15 min, the precipitated manganese dioxide is filtered off and washed with 40 cm$^3$ of a 1:3 mixture of ethanol-water. The filtrate is neutralized with 5 cm$^3$ of 10% sulfuric acid is (pH~6–7), then the ethanol is evaporated at diminished pressure. The residue is cooled to 15–20° C. and acidified with 12 cm$^3$ of 10% sulfuric acid (pH~2). The crystalline solution is stirred for 20 min. then filtered, washed with water and dried at 50° C. till the weight is constant to yield 2.5 g (64.6%) of crude title compound. Mp: 177–190° C.

EXAMPLE 6

17β-Hydroxy-17α-methyl-1,3-seco-2-nor-5α-androstane-1,3-diacid 5 g (11.4 mmol) of crude 17β-hydroxy-17α-methyl-1-(1,3-dihydro-3-oxo-2H-indol-2-ylidene)-1,3-seco-2-nor-5α-androstane-3-acid, obtained in Example 2. is dissolved in 40 cm$^3$ of acetone and 0.8 g (20 mmol) of sodium hydroxide in 40 cm$^3$ of water is added. 5.4 g (34.2 mmol. 3.0 equivalent) of potassium permanganate in 90 cm$^3$ of water is added to the reaction mixture over a period of 30 min. keeping the temperature at 20–30° C. After stirring for 15 min. the precipitated manganese dioxide is filtered off and washed with 40 cm$^3$ of a 1:3 mixture of acetone-water. The filtrate is neutralized with 5 cm$^3$ of 10% sulfuric acid is (pH~6–7), then the acetone is evaporated at diminished pressure. The residue is cooled to 15–20° C. and acidified with 12 cm$^3$ of 10% sulfuric acid (pH~2). The crystalline solution is stirred for 20 min. then filtered, washed with water and dried at 50° C. till the weight is constant to yield 2.7 g (69.8%) of crude title compound. Mp: 176–189° C.

EXAMPLE 7

17β-Hydroxy-17α-methyl-1,3-seco-2-nor-5α-androstane-1,3-diacid 469.0 g of crude 17 β-hydroxy-17α-methyl-1-(1,3-dihydro-3-oxo-2H-indol-2-ylidene)-1,3-seco-2-nor-5α-androstane-3-acid, obtained in Example 2, is added to a stirred mixture of 60.0 g (1.5 mol) of sodium hydroxide in 3.0 dm$^3$ of water and 6.5 dm$^3$ of tertiary-butanol. After dissolving the starting material the pH of the solution is checked (pH=12–13). 433 g (2.74 mol) of potassium permanganate in 7.2 dm$^3$ of water is added to the reaction mixture over a period of 2 h. keeping the temperature at 20–30° C. with cooling. During the addition of the reagent the reaction mixture turns dark brown and manganese dioxide precipitates. After addition of two third of the starting material 400 cm$^3$ of 10% sodium hydroxide is added to the reaction mixture and after stirring for 5 min. the pH is checked (pH=12), then the addition of the reagent is continued. After the addition the reaction mixture is stirred for 30 min at 20–30° C. Then the reaction mixture is filtered and the manganese dioxide is washed with 4.0 dm$^3$ of a 1:3 mixture of tertiary-butanol-water. The filtrate is neutralized with 520 cm$^3$ of 10% sulfuric acid is (pH~6–7), then the tertiary-butanol is evaporated at diminished pressure. The residue is cooled to 18–20° C. and after 20 min stirring the precipitated crystals (the by-products of the previous and the present reaction) are filtered off and washed with 200 cm$^3$ of water. The filtrate is acidified with 1300 cm$^3$ of 10% sulfuric acid (pH~2) at 20–25° C. The crystalline solution is stirred for 15 min. then filtered, washed with water and dried at 50° C. till the weight is constant to yield 301 g (83.0%) of crude title compound. Mp: 176–190° C.

EXAMPLE 8

17β-Hydroxy-17α-methyl-1,3-seco-2-nor-5α-androstane-1,3-diacid 469 g of recrystallized 17β-hydroxy-17α-methyl-1-(1,3-dihydro-3-oxo-2H-indol-2-ylidene)-1,3-seco-2-nor-5α-androstane-3-acid obtained in Example 1. is added to a stirred mixture of 60 g (1.50 mol) of sodium hydroxide in 3.0 dm³ of water and 6.5 dm³ of tertiary-butanol. After dissolving the starting material the pH of the solution is checked (pH=12–13). 433 g (2.74 mol) of potassium permanganate in 7.2 dm³ of water is added to the reaction mixture over a period of 2 h. keeping the temperature at 20–30° C. with cooling. During the addition of the reagent the reaction mixture turns dark brown and manganese dioxide precipitates. After addition of two third of the starting material 400 cm³ of 10% sodium hydroxide is added to the reaction mixture and after stirring for 5 min, the pH is checked (pH=12), then the addition of the reagent is continued. After the addition the reaction mixture is stirred for 30 min at 20–30° C. Then the reaction mixture is filtered and the manganese dioxide is washed with 4.0 dm³ of a 1:3 mixture of tertiary-butanol-water. The filtrate is neutralized with 520 cm³ of 10% sulfuric acid is (pH=6), then the tertiary-butanol is evaporated at diminished pressure. The residue is cooled to 18–20° C. and after 20 min stirring the precipitated crystals (the by-products of the previous and the present reaction) are filtered off and washed with 200 cm³ of water. The filtrate is acidified with 1300 cm³ of 10% sulfuric acid (pH=2) at 20–25° C. The crystalline solution is stirred for 15 min, then filtered, washed with water and dried at 50° C. till the weight is constant to yield 359 g (99.0%) of crude title compound. Mp: 178–190° C.

EXAMPLE 9

17β-Hydroxy-17α-methyl-1,3-seco-2-nor-5α-androstane-1,3-diacid 326 g of the crude product obtained in Example 7 is added to mixture of 2.6 dm³ of dichloromethane and 650 cm³ of acetone over a period of 20 min and the obtained suspension is stirred for 3 h. then filtered. washed with a mixture of 400 cm³ of dichloromethane and 100 cm³ of acetone and dried at 50° C. to yield 2 g (71%) of the title compound. Mp: 249–251° C. $[\alpha]_D^{25}=-18.4°$ (c=1, methanol).

EXAMPLE 10

17β-Hydroxy-17α-methyl-1,3-seco-2-nor-5α-androstane-1,3-diacid 25 g of the crude product obtained in Example 7 is dissolved in 530 cm³ of acetone at reflux temperature, treated with 1.0 g of charcoal. filtered, then the filtrate is concentrated to a volume of 60 cm³. The concentrated mixture is cooled to 10° C. and kept at this temperature for 2 h, then the precipitated crystalline product is filtered off, washed with 20 cm³ of cold acetone and dried to yield 20.1 g (80.4%) of the title compound. Mp 248–250° C.

EXAMPLE 11

17β-Hydroxy-17α-methyl-1,3-seco-2-nor-5α-androstane- 1,3-diacid 3 g (6.4 mmol) of 17β-hydroxy-17α-methyl-1-(5-chloro-1,3-dihydro-3-oxo-2H-indol-2-ylidene)-1,3-seco-2-nor-5α-androstane-3-acid, obtained in Example 3. is added to a stirred mixture of 0.5 a (12.5 mmol) of sodium hydroxide in 20 cm³ of water and 50 cm³ of tertiary-butanol. 3.0 g (19 mmol, 3.0 equivalent) of potassium permanganate in 50 cm³ of water is added to the reaction mixture over a period of 30 min. keeping the temperature at 20–30° C. After stirring for 15 min the precipitated manganese dioxide is filtered and washed with 30 cm³ of a 1:3 mixture of tertiary-butanol-water. The filtrate is neutralized with 3 cm³ of 10% sulfuric acid is (pH~6–7), then the tertiary-butanol is evaporated at diminished pressure. The residue is cooled to 15–20° C. and acidified with 9 cm³ of 10% sulfuric acid (pH~2). The crystalline solution is stirred for 20 min. then filtered, washed with water and dried at 50° C. till the weight is constant to yield 2.0 g (93.0%) of crude title compound. Mp: 178–190° C.

What we claim is:

1. A secoindoxylidene carboxylic acid of the formula (II)

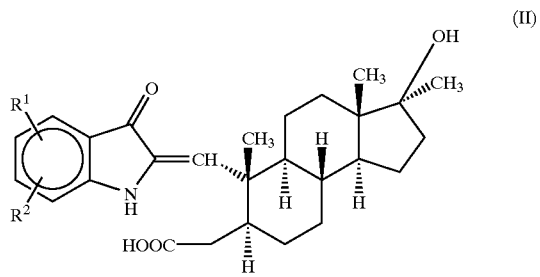

wherein $R^1$ and $R^2$ independently are $C_1$–$C_4$ alkyl or alkoxy group, hydrogen or halogen atom.

2. 17β-hydroxy-17α-methyl-1-(1,3-dihydro-3-oxo-2H-indol-2-ylidene)-1,3-seco-2-nor-5α-androstane-3-acid as in claim 1.

3. 17β-hydroxy-17α-methyl-1-(5-chloro-1,3dihydro-3-oxo-2H-indol-2-ylidene)-1,3-seco-2-nor-5α-androstane-3-acid as claimed in claim 1.

4. Process for the synthesis of a 17β-hydroxy-17α-methyl-1,3-seco-2-nor-5α-androstane-3-acid of formula (I)

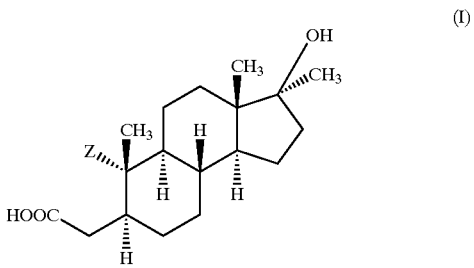

wherein the meaning of Z is carboxyl or formyl group—characterized by reacting the 17β-hydroxy-17α-methyl-5α-androstane-3-one (mestanolone) of formula (III)

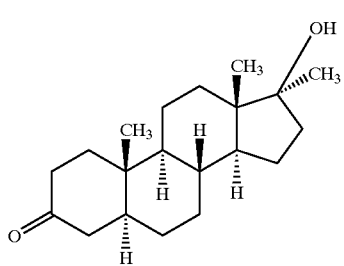

with an aromatic nitro-aldehyde of formula (IV)

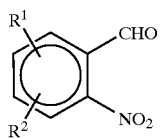

wherein $R^1$ and $R^2$ independently are $C_1$–$C_4$ alkyl or alkoxy group, hydrogen or halogen atom—in a $C_1$–$C_4$ alcohol in the presence of aqueous alkali metal hydroxide solution,
the obtained secoindoxylidene carboxylic acid of formula (II)

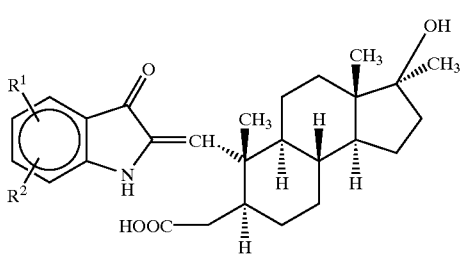

wherein the meaning of $R^1$ and $R^2$ as defined above—is separated from the reaction mixture after acidifying, in given case is recrystallized from a $C_1$–$C_4$ alcohol or $C_3$–$C_5$ ketone and oxidized using i) for the synthesis of 17β-hydroxy-17α-methyl-1,3-seco-2-nor-5α-androstane-3-acid derivative of formula (I), wherein Z is carboxyl group, at 15–40° C. 2.5–5 mol equivalent, or ii) for the synthesis of 17β-hydroxy-17α-methyl-1,3-seco-2-nor-5α-androstane-3-acid of formula (I), wherein Z is formyl group, at 15–30° C., 1–1.5 mol equivalent alkali metal permanganate in a mixture of $C_1$–$C_5$ alcohol or $C_3$–$C_6$ ketone and aqueous alkali metal hydroxide.

5. The process in claim 4, characterized by reacting the 17β-hydroxy-17α-methyl-methyl-5α-androstane-3-one of formula (III) and the aromatic aldehyde of formula (IV)—wherein the meaning of $R^1$ and $R^2$ as defined above—in a mixture of methanol and aqueous potassium hydroxide.

6. The process in claim 4, characterized by using 2-nitro-benzaldehyde as aromatic aldehyde of formula (IV).

7. The process in claim 4, characterized by using 5-chloro-2-nitro-benzaldehyde as aromatic aldehyde of formula (IV).

8. The process in claim 4, characterized by carrying out the oxidation of secoindoxylidene carboxylic acid of formula (II)—wherein the meaning of $R^1$ and $R^2$ as defined in claim 4—in a mixture of acetone and aqueous sodium hydroxide.

9. The process in claim 4, characterized by carrying out the oxidation of secoindoxylidene carboxylic acid of formula (II)—wherein the meaning of $R^1$ and $R^2$ as defined in claim 4—in a mixture of ethanol and aqueous sodium hydroxide.

10. The process in claim 4, characterized by carrying out the oxidation of secoindoxylidene carboxylic acid of formula (II)—wherein the meaning of $R^1$ and $R^2$ as defined in claim 4—in a mixture of tertiary-butanol and aqueous sodium hydroxide.

11. The process in claim 4, characterized by carrying out the oxidation of secoindoxylidene carboxylic acid derivatives of formula (II)—wherein the meaning of $R^1$ l and $R^2$ as defined in claim 4—with potassium permanganate.

* * * * *